United States Patent [19]

Skribiski

[11] Patent Number: 4,790,831
[45] Date of Patent: Dec. 13, 1988

[54] TORQUE-CONTROL CATHETER

[75] Inventor: Robert P. Skribiski, Irvine, Calif.

[73] Assignee: Baxter Travenol Laboratories, Inc., Deerfield, Ill.

[21] Appl. No.: 31,867

[22] Filed: Mar. 30, 1987

[51] Int. Cl.⁴ ............................................. A61M 25/00
[52] U.S. Cl. ..................................... 604/282; 604/280; 604/264
[58] Field of Search ............................... 604/280–283, 604/264, 163

[56] References Cited

U.S. PATENT DOCUMENTS

| | | |
|---|---|---|
| 882,292 | 3/1908 | Brown . |
| 1,596,754 | 8/1926 | Moschelle . |
| 3,314,449 | 4/1967 | Krone et al. ........................ 138/125 |
| 3,498,286 | 3/1970 | Polanyi et al. ........................ 128/2 |
| 3,860,040 | 1/1975 | Sullivan ............................... 138/124 |
| 3,948,273 | 4/1976 | Sanders ............................... 604/280 |
| 4,150,673 | 4/1979 | Watt .................................... 604/408 |
| 4,249,971 | 2/1981 | Yap et al. ............................ 156/143 |
| 4,261,390 | 4/1981 | Belofski .............................. 138/125 |
| 4,306,563 | 12/1981 | Iwatacheako ...................... 128/349 |
| 4,307,723 | 12/1981 | Finney ................................. 604/281 |
| 4,430,083 | 2/1984 | Ganz et al. .......................... 604/283 |
| 4,547,193 | 10/1985 | Rydell ................................. 604/282 |
| 4,551,140 | 11/1985 | Shinohara ........................... 604/280 |
| 4,581,390 | 4/1986 | Flynn .................................. 604/280 |
| 4,627,844 | 12/1986 | Schmitt ............................... 604/280 |
| 4,682,981 | 7/1987 | Suzuki et al. ....................... 604/283 |

Primary Examiner—C. Fred Rosenbaum
Assistant Examiner—Gene B. Kartchner
Attorney, Agent, or Firm—Loyal M. Hanson

[57] ABSTRACT

A catheter includes an elongated tube having a size and shape adapted to be inserted into the cardiovascular system that is composed of a material having a modulus of elasticity providing stiffness to enhance catheter torque control, and a sheath coaxially disposed over and bonded to the tube that is composed of a biocompatible material having a modulus of elasticity providing softness to reduce catheter trauma to the cardiovascular system. An outer portion of the tube defines a plurality of longitudinally-extending ribs protruding radially outward at circumferentially spaced-apart locations, each one of the ribs having a cross sectional area that increases radially inward, for engaging the sheath circumferentially, for defining an outer surface of the tube that generally faces radially outward toward the sheath to thereby facilitate a closely-confronting relationship between the sheath and tube over substantially the entire outer surface, and for extending the outer surface over an enlarged area to thereby facilitate a better bond of the sheath to the tube.

23 Claims, 1 Drawing Sheet

TORQUE-CONTROL CATHETER

BACKGROUND OF THE INVENTION

1. Technical Field

This invention relates generally to catheters adapted to be inserted into the cardiovascular system, and more particularly to a new and improved catheter construction providing better torque control.

2. Background Information

"Torque control" refers to the ability of a catheter to transmit twisting forces along its length, and satisfactory catheter performance often depends on this ability. It enables carefully controlled maneuvering within the cardiovascular system by skilled manipulation of the catheter at the proximal end. Thus, catheter torque control is of recognized significance and each detail of construction enhancing this attribute of corresponding importance.

Apart from torque control, however, the catheter must also exhibit flexibility and softness, these attributes helping to avoid trauma to the cardiovascular system when the catheter is introduced. However, the materials and constructions utilized in existing catheter designs for flexibility and softness often exhibit too little torque control. Instead of transmitting twisting forces as desired, the catheter deforms elastically, and this makes manipulation within the cardiovascular system more difficult. Although reinforced catheters exist, such as those utilizing a braided layer, these are more complex to fabricate and more costly.

Therefore, it is desirable to have a new and improved catheter that overcomes this concern—one combining flexibility and softness in a construction exhibiting improved torque control. In addition, it is desirable that this be accomplished in a catheter construction adapted to be conveniently and inexpensively fabricated.

SUMMARY OF THE INVENTION

This invention recognizes the problems associated with the prior art and provides a new and improved catheter with the desired attributes.

Briefly, the above mentioned and further objects of the present invention are realized by providing a catheter having a catheter body formed from a soft outer sheath coextruded over a stiffer core or inner tube having a multilobal cross section.

The elongated inner tube has a size and shape adapted to be inserted into a cardiovascular system, and it is composed of a material having a modulus of elasticity providing stiffness to enhance catheter torque control. The outer sheath is coaxially disposed over and bonded to the tube, and it is composed of a biocompatible material having a modulus of elasticity providing softness to reduce catheter trauma to the cardiovascular system.

An outer portion of the tube engages and/or is bonded to the sheath. The outer portion of the tube defines a plurality of longitudinally-extending ribs that protrude radially outwardly at circumferentially spaced-apart locations on the tube. Each one of the ribs has a cross sectional area that increases radially inwardly, and thus configured, the outer portion engages the sheath circumferentially.

In addition, the outer portion defines an outer surface of the tube that generally faces radially outwardly toward the sheath to thereby facilitate a closely-confronting relationship between the sheath and tube over substantially the entire outer surface. Moreover, the outer portion extends the outer surface over an enlarged area to thereby facilitate a better bond of the sheath to the tube.

A method of making the catheter includes the steps of extruding an elongated tube as described above, coextruding a sheath coaxially over the tube, and bonding the sheath to the tube. In one form of the invention, an extrudable, hot melt, adhesive material, such as the copolymer ethylene-vinyl-acetate (EVA), is coextruded between an inner tube composed of a nylon or a thermoplastic polyester material, such as the material commonly called PET, and an outer sheath composed of a polyethylene, polyurethane, or polyester-polyamide copolymer. Both the tube and sheath adhere well to the EVA so that a superior bond is produced in a conveniently and inexpensively fabricated structure having the desired attributes.

Thus, the catheter of this invention overcomes many concerns of the prior art by a novel combination of core and sheath coextruded from materials and in a manner providing flexibility and softness, as well as improved torque control. It does so with tubing profiles of various geometric shapes covered with a sheath of different plastic composition to achieve torque control without the use of a reinforcing medium such as a metallic wire braid. In addition, the catheter lends itself to convenient and inexpensive fabrication.

The above mentioned and other objects and features of this invention and the manner of attaining them will become apparent, and the invention itself will be best understood, by reference to the following description taken in conjunction with the accompanying illustrative drawings.

DESCRIPTION OF THE PREFERRED EMBODIMENTS

Figure 1:
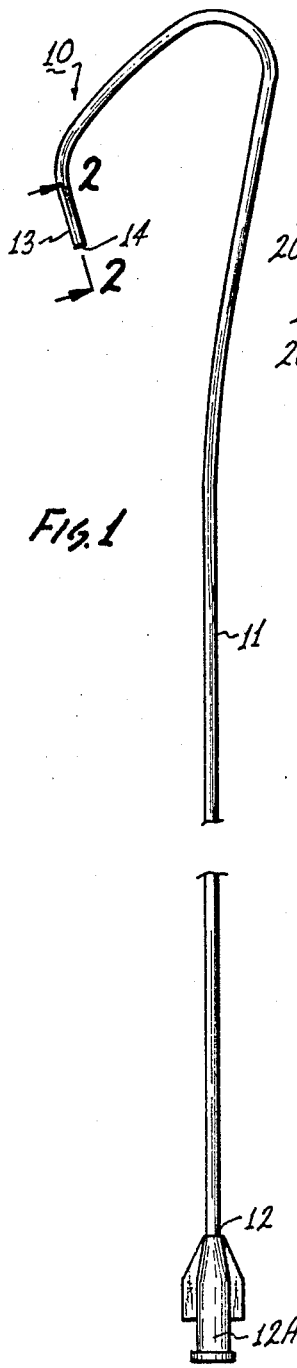
FIG. 1 of the drawings is a plan view of an angiography catheter constructed according to the invention.

Referring now to the drawings, and particularly to FIG. 1, there is shown a new and improved catheter 10 constructed according to the invention. Although the catheter 10 is designed for use as a one hundred centimeter long angiography catheter with a Judkins curve and 8 French tip, the inventive concepts disclosed are equally applicable to any of various other catheters adapted to be introduced into the cardiovascular system.

Figure 2:
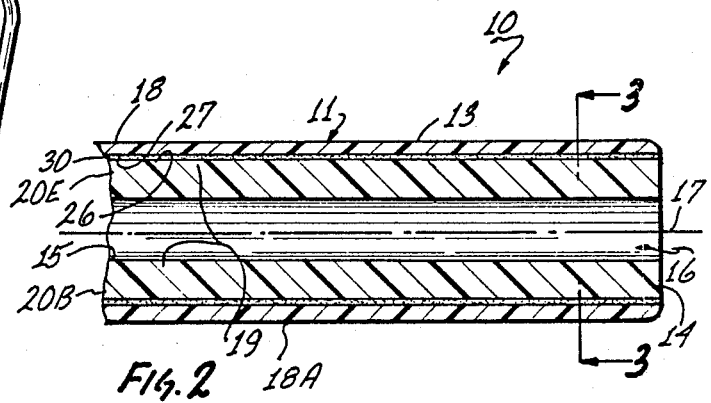
FIG. 2 is an enlarged longitudinal cross section of the distal end portion of the catheter tube taken on line 2—2 of FIG. 1.

Generally, the catheter 10 includes a catheter body 11, illustrated foreshortened for convenience, that extends from a proximal end portion 12 at or within a proximal fitting 12A to a distal end portion 13 terminating at a distal or terminal end 14 (FIG. 1). The catheter body 11 includes an elongated inner tube 15 defining a lumen 16 that extends in a conventional manner within the tube 15 along an axis 17, the axis of elongation of tube 15, and an outer sheath 18 disposed coaxially over and bonded to the tube 15 (FIG. 2).

Only the distal end portion 13 of the catheter tube 11 is shown in cross section because the illustrated catheter 10 employs a catheter body 11 that has a generally uniform cross section throughout its length. Another embodiment (not shown) has a cross section that varies over its length to provide variances in torque control at selected regions along its length. This feature enables flexibility in catheter design to achieve particular torque control characteristics for different catheter applications. In addition, a catheter constructed according to the invention may have more than one lumen.

The tube 15 has a size and shape adapted to be inserted into a cardiovascular system. It is composed of a material having a modulus of elasticity providing stiffness to enhance catheter torque control, while the sheath 18 is composed of a biocompatible material having a modulus of elasticity providing softness to reduce catheter trauma to the cardiovascular system. In addition, the sheath 18 has an outer surface 18A that defines at least a portion of the outer surface of the catheter 10.

Figure 3:
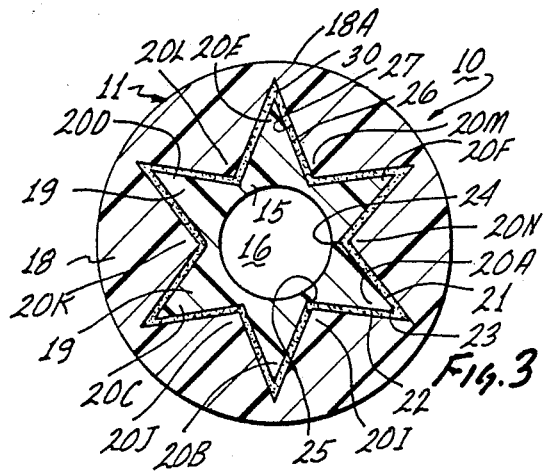
FIG. 3 is a further enlarged transverse cross section of the distal end portion taken on line 3—3 of FIG. 2.

An outer portion 19 of the tube 15 defines a plurality of longitudinally-extending ribs 20A–F as shown in FIG. 3. The outer portion 19 is designated adjacent ribs 20C and 20D, but it is the outer portion of tube 15 extending fully around the circumference of tube 15 to define all of the ribs 20A–F. The ribs 20A–F thus defined protrude radially outward at circumferentially spaced apart locations on the tube 15 to provide a superior interface between the tube 15 and the sheath 18. They define corresponding longitudinally extending spaces between each adjacent pair of the ribs, into which longitudinally extending, inwardly facing ribs 20I–N of the sheath 18 extend.

Although the catheter 10 employs a tube 15 having a six-pointed, star-shaped cross section, various other multilobal cross sections may be used within the inventive concepts described. In addition, the ribs 20A–F need not have similar shapes. In the catheter 10, however, each of the ribs 20A–F is similar so that only the rib 20A will be described in detail.

The rib 20A extends longitudinally along the tube generally parallel to the axis 17, and it includes a pair of oppositely facing sides 21 and 22 that converge radially outward to a vertex 23 (FIG. 2). The sides 21 and 22 extend inwardly from the vertex 23 to respective ones of a pair of points 24 and 25 (the base points of the valleys between rib 20A and the adjacent ribs 20B and 20F) where the sides 21 and 22 meet the sides of the adjacent ribs 20A and 20F. So configured, the rib 20A has a cross sectional area that increases radially inward toward the lumen 16.

Thus, the tube 15 and the sheath 18 fit together in an interlocking relationship with the ribs 20A–H of the tube 15 engaging the ribs 20I–N of the sheath 18, separated only by the layer 30, so that the outer portion 19 performs several functions. First, it interlocks the sheath 18 circumferentially to transmit twisting forces to the sheath so that when the tube 15 twists, the sheath 18 twists also. Similarly, the outer portion 19 resists torsion applied to the sheath 18. In addition, it defines an outer surface 26 of the tube 15 extending fully around the tube (defined by the sides of the ribs 20A–F) that generally faces radially outwardly toward the sheath 18.

The outer surface 26 generally faces radially outwardly in the sense that it generally faces away from the lumen 16, and this facilitates a closely-confronting relationship between an inner surface 27 of the sheath 18 and the tube 15 over substantially the entire outer surface 26. In other words, there are no undercut regions facing toward the lumen into which the sheath 18 must be forced to achieve the closely-confronting relationship. Thus, the inner surface 27 of the sheath 18 closely conforms to the outer surface 26 of the tube 15, and this facilitates fabrication by coextrusion of the tube 15 and sheath 18.

Moreover, the outer portion 19 serves to extend the outer surface 26 over an enlarged area, i.e. the area of the outer surface 26 is greater than if it were, for example, cylindrically-shaped. Thus, the area of the interface between the sheath 18 and the tube 15 is correspondingly increased, and this results in a better or stronger bond between the sheath 18 and the tube 15.

In the catheter 10, a thin film or layer 30 (FIGS. 2 and 3) is employed to effect the bond, although a parent bond between the tube 15 and the sheath 18 may be employed depending on the materials used and attributes desired. The thickness of layer 30 is exaggerated for illustrative convenience, it preferably being no more than adequate to adhere to both the tube 15 and the sheath 18 to bond the two together, and it generally conforms to the shape of the outer surface 26 and does not fill the valley between the ribs 20A–F. Thus, the layer 30 bonds the outer surface 26 of the tube 15 to the inner surface 27 of the sheath 18 without impairing the interlocking relationship accomplished with the ribs 20A–F. In addition, the region between the tube 15 and the sheath 18 is not reinforced.

Figure 4:
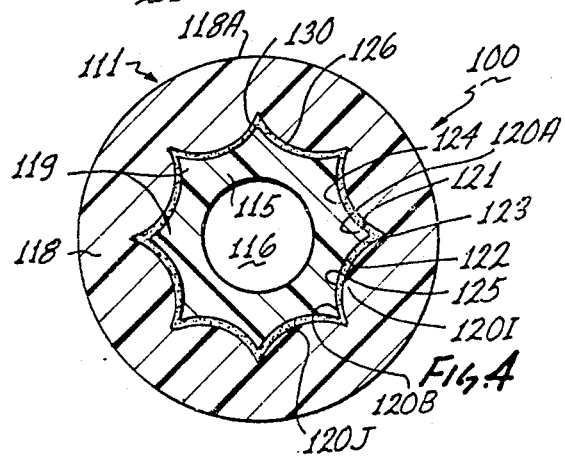
FIG. 4 is an enlarged transverse cross section similar to FIG. 3 of another embodiment.

Another catheter constructed according to the invention, catheter 100, is illustrated in FIG. 4. The catheter 100 employs an inner tube 115 having a different cross sectional shape than the the inner tube 15 of the catheter 10. Otherwise, the catheter 100 is generally similar to the catheter 10, so that only the dissimilar aspects of the inner tube 115 will be described.

For convenience, reference numerals in FIG. 4 are increased by one hundred over those designating similar features of the catheter 10 in FIGS. 1–3. In addition, to emphasize that the layer 130 does not fill the valley between adjacent ones of ribs 120A–H, it is illustrated less exaggerated than the layer 30 in FIG. 3. Also, for illustrative convenience, many of the ribs are not numbered.

The tube 115 includes an outer portion 119 that defines a plurality of longitudinally-extending ribs, of which ribs 120A and 120B are numbered. Similar to the ribs 20A–F of catheter 10, the ribs of catheter 100 protrude radially outward at circumferentially spaced apart locations on the tube 115 to provide a superior interface between the tube 115 and the sheath 118. The multilobal cross section of the tube 115 is somewhat different than that of the catheter 10, however. It defines eight lobes or ribs, and this increased number serves to provide a desired amount of circumferential interlock of the sheath 118 with ribs that do not extend outwardly as far.

In other words, like rib 20A of the catheter 10, the rib 120A includes a pair of oppositely facing sides 121 and 122 that converge radially outwardly from a pair of points 124 and 125 to a vertex 123. However, the vertex 123 does not extend radially outward relative to the points 124 and 125 as far as the vertex 23 of catheter 10 does relative to the points 24 and 25, and this results in a tube 115 of more uniform thickness and correspondingly different operational characteristics. As many as twenty or more ribs are employed in other embodiments of the invention (not shown) to attain the precise characteristics desired for specific applications.

The catheter 100 also differs from the catheter 10 in that the sides 121 and 122 are curved. This results in a generally continuous outer surface 126 between the vertices of adjacent ribs to which to bond the sheath. In this regard, the outer surface 126 is generally continuous in the sense that it curves gradually from vertex to vertex of adjacent ones of the ribs 120A–H, instead of having an abrupt change of direction as occurs at points 24 and 25 in the catheter 10. Thus, there is less stress concentration at the base of the valley between adjacent ribs, i.e., such as at the points 124 and 125, in comparison to the stress in the vincinity of such points as points 24 and 25 in catheter 10. In addition, the sheath 118 is more easily disposed in a closely-confronting relationship to the outer surface 126.

Fabrication of either the catheter 10 or the catheter 100 proceeds in a similar manner using injection molding techniques. With reference to the catheter 10, the method of fabricating the catheter includes using suitable extrusion molding equipment to coextrude the tube 15 and the sheath 18. Preferably, the coextrusion equipment includes three orifices for this purpose, one for each of the tube 15, the sheath 18, and the adhesive layer 30, the tube, sheath, and adhesive layer being extruded coaxially in the desired configuration.

Thus, the method comprises extruding an elongated tube defining at least one lumen extending generally along an axis of elongation of the tube. This is done using a material having a modulus of elasticity providing stiffness to enhance catheter torque control, such as nylon, and so that the tube includes an outer portion defining a plurality of longitudinally-extending ribs protruding radially outward at circumferentially spaced-apart locations on the tube, each one of the ribs having a cross sectional area that increases radially inward.

The method includes coextruding a sheath coaxially over the tube from a biocompatible material having a modulus of elasticity providing softness to reduce catheter trauma to the cardiovascular system, such as the polyester-polyamide copolymer mentioned above.

The tube 15 and the sheath 18 may employ materials that adhere together in a parent bond. However, the method of this invention may include coextruding a layer of adhesive material between the tube 15 and the sheath 18 to accomplish the bonding function, and this step may include use of an extrudable, hot meld adhesive material as mentioned above.

Fabrication in this manner results in the catheter 10 described above, wherein the outer portion engages, in the absence of a separate adhesive layer, the sheath circumferentially, defines an outer surface of the tube that generally faces radially outward toward the sheath to thereby facilitate a closely-confronting relationship between the sheath and tube over the entire outer surface, and increases the surface area of the outer surface to which the sheath is bonded.

The combination of various geometric shapes covered with a sheath of different plastic composition achieves flexibility and softness as well as torque control, and without the use of a reinforcing medium such as a metallic wire braid. In addition, the catheter is convenient and inexpensive to fabricate using known extrusion techniques.

Although an exemplary embodiment of the invention has been shown and described, many changes, modifications, and substitutions may be made by one having ordinary skill in the art without necessarily departing from the spirit and scope of this invention.

What is claimed is:

1. A catheter, comprising:
   an elongated flexible tube defining at least one lumen extending longitudinally within the tube, the tube having a size and shape adapted to be inserted into a cardiovascular system, which tube is composed of a material having a modulus of elasticity providing stiffness to enhance catheter torque control;
   a biocompatible sheath disposed over the tube, which sheath is composed of a biocompatible material having a modulus of elasticity providing softness to reduce catheter trauma to the cardiovascular system;
   the tube being stiffer than the sheath; and
   the tube having a plurality of longitudinally-extending ribs protruding radially outward at circumferentially spaced-apart locations on the tube and having longitudinally extending spaces between each adjacent pair of the ribs, said sheath having longitudinally extending inwardly facing ribs received in said spaces, respectively, to form an interlocking relationship with the ribs of the tube, each one of the ribs having a cross sectional area that increases inwardly, for engaging the sheath circumferentially, for defining an outer surface of the tube that generally faces outwardly toward the sheath to thereby facilitate a closely-confronting relationship between the sheath and tube over substantially the entire outer surface, and for extending the outer surface over an enlarged area to thereby facilitate a better bond of the sheath to the tube.

2. A catheter as recited in claim 1, wherein:
   the sheath is bonded to the tube with a parent bond.

3. A catheter as recited in claim 1, further comprising:
   bonding means, including a thin layer of adhesive material disposed between the tube and the sheath, for bonding the sheath to the tube.

4. A catheter as recited in claim 7, wherein:
   the thin layer of adhesive material is composed of an extrudable, hot melt adhesive material.

5. A catheter as recited in claim 4, wherein:
   the thin layer of adhesive material is composed of an ethylene-vinyl-acetate material.

6. A catheter as recited in claim 1, wherein:
   the tube has a cross sectional area that is generally uniform throughout the length of the tube.

7. A catheter as recited in claim 1, wherein:
   the tube has a generally star-shaped cross section.

8. A catheter as recited in claim 1, wherein:
   each one of the ribs has a pair of oppositely-facing, radially-converging sides that converge outwardly to a vertex of the rib; and
   each one of the sides is generally planar.

9. A catheter as recited in claim 1, wherein:
   each one of the ribs has a pair of oppositely-facing, radially-converging sides that converge outwardly to a vertex of the rib; and
   each one of the sides curves concavely to define a generally continuous surface extending from the vertex of the rib to a respective vertex of an adjacent rib.

10. A catheter as recited in claim 1, wherein: the tube is composed of a nylon material.

11. A catheter as recited in claim 10, wherein: the tube is composed of a PET material.

12. A catheter as recited in claim 1, wherein: the sheath is composed of a material selected from the group consisting of a polyester material and a polyurethane material.

13. A catheter as recited in claim 12, wherein: the sheath is composed of a polyester-polyamide copolymer material.

14. A catheter as recited in claim 1, wherein: the sheath has an outer surface which defines at least a portion of the outer surface of the catheter.

15. A catheter as recited in claim 1, wherein: the ribs of the tube and the ribs of the sheath engage.

16. A catheter as recited in claim 1, wherein: an adhesive material bonds the tube to the sheath and the ribs of the tube and the ribs of the sheath are spaced apart solely by said adhesive material.

17. A catheter as recited in claim 1, wherein: the region between the tube and the sheath is unreinforced.

18. A catheter, comprising:
an elongated tube defining a lumen extending along an axis of elongation of the tube, the tube having a size and shape adapted to be inserted into a cardiovascular system, which tube is composed of a material having a modulus of elasticity providing stiffness to enhance catheter torque control;
a biocompatible sheath disposed over and bonding to the tube, which sheath is composed of a biocompatible material having a modulus of elasticity providing softness to reduce catheter trauma to the cardiovascular system;
the tube being stiffer than the sheath; and
sheath engaging means, including an outer portion of the tube having a plurality of longitudinally-extending ribs protruding radially outward at circumferentially spaced-apart locations on the tube, each one of the ribs having a cross sectional area that increases radially inwardly, for engaging the sheath circumferentially, for defining an outer surface of the tube that generally faces radially outwardly toward the sheath to thereby facilitate a closely-confronting relationship between the sheath and tube over substantially the entire outer surface, and for extending the outer surface over an enlarged area to thereby facilitate a better bond of the sheath to the tube.

19. A catheter as recited in claim 1, wherein: the catheter has a curved distal end portion.

20. A catheter as recited in claim 19, wherein: the curved distal end portion is configured to define a Judkins curve.

21. A catheter as recited in claim 1, further comprising:
a proximal fitting.

22. A method, comprising:
providing a catheter that includes an elongated flexible tube composed of a material having a modulus of elasticity providing stiffness to enhance catheter torque control and a sheath disposed over the tube that is composed of a biocompatible material having a less stiff modulus of elasticity providing softness to reduce catheter trauma to the cardiovascular system, which tube has a plurality of longitudinally-extending ribs protruding radially outward at circumferentially spaced-apart locations on the tube and having longitudinally extending spaces between each adjacent pair of the ribs, and which sheath has longitudinally extending inwardly facing ribs received in said spaces, respectively, to form an interlocking relationship with the ribs of the tube, each one of the ribs having a cross sectional area that increases inwardly, for engaging the sheath circumferentially, for defining an outer surface of the tube that generally faces outwardly toward the sheath to thereby facilitate a closely-confronting relationship between the sheath and tube over substantially the entire outer surface, and for extending the outer surface over an enlarged area to thereby facilitate a better bond of the sheath to the tube; and
inserting the catheter into the cardiovascular system.

23. A method as recited in claim 22, where in the step of inserting the catheter includes:
twisting the catheter.

* * * * *